United States Patent
Engelbart et al.

(10) Patent No.: US 9,360,459 B2
(45) Date of Patent: Jun. 7, 2016

(54) POROSITY INSPECTION SYSTEM FOR COMPOSITE STRUCTURE WITH NON-PARALLEL SURFACES

(71) Applicant: The Boeing Company, Chicago, IL (US)

(72) Inventors: Roger W. Engelbart, St. Louis, MO (US); Christopher Mark Vaccaro, O'Fallon, MO (US); Nancy L. Wood, St. Louis, MO (US)

(73) Assignee: THE BOEING COMPANY, Chicago, IL (US)

( * ) Notice: Subject to any disclaimer, the term of this patent is extended or adjusted under 35 U.S.C. 154(b) by 427 days.

(21) Appl. No.: 13/897,007

(22) Filed: May 17, 2013

(65) Prior Publication Data
US 2014/0338453 A1 Nov. 20, 2014

(51) Int. Cl.
G01N 29/04 (2006.01)
G01N 29/11 (2006.01)
G01B 17/02 (2006.01)
G01N 29/48 (2006.01)

(52) U.S. Cl.
CPC .............. *G01N 29/043* (2013.01); *G01B 17/02* (2013.01); *G01N 29/11* (2013.01); *G01N 29/48* (2013.01); *G01N 2291/015* (2013.01); *G01N 2291/0231* (2013.01); *G01N 2291/02854* (2013.01); *G01N 2291/2694* (2013.01)

(58) Field of Classification Search
CPC .......... G01N 29/11; G01N 2291/2694; G01N 2291/0231; G01N 29/4418; G01N 29/4427; G01N 15/088; G01N 29/043; G01M 11/3181
USPC ..................................................... 73/38, 600
See application file for complete search history.

(56) References Cited

U.S. PATENT DOCUMENTS

| 7,353,709 | B2 | 4/2008 | Kruger et al. |
| 7,362,427 | B2 | 4/2008 | Fayolle et al. |
| 7,362,437 | B2 | 4/2008 | Engelbart et al. |
| 7,389,693 | B2 | 6/2008 | Reed et al. |
| 7,424,818 | B2 * | 9/2008 | Vaccaro ................. G01N 29/30 73/1.86 |
| 7,617,730 | B2 * | 11/2009 | Georgeson ......... G01N 29/0645 73/602 |
| 7,757,558 | B2 * | 7/2010 | Bossi .................... G01N 29/11 73/609 |
| 7,762,120 | B2 | 7/2010 | Vaccaro et al. |
| 8,826,740 | B2 | 9/2014 | Bergman |
| 8,934,703 | B2 * | 1/2015 | Tsubaki ............ G01N 29/0654 382/141 |

(Continued)

FOREIGN PATENT DOCUMENTS

EP 2487487 A1 8/2012

OTHER PUBLICATIONS

Engelbart et al., "Porosity Inspection System for Composite Structures," U.S. Appl. No. 13/568,985, filed Aug. 7, 2012, 57 pages.

(Continued)

*Primary Examiner* — Freddie Kirkland, III
(74) *Attorney, Agent, or Firm* — Yee & Associates, P.C.

(57) ABSTRACT

A method and apparatus for inspecting a composite structure. A thickness profile of a portion of a region of a composite structure is identified. The region has a cross-section with non-parallel surfaces. An estimated thickness for a location within the region and outside of the portion is identified using the thickness profile. An indication of whether the location has undesirable porosity is generated based on information about attenuation of response sound signals and the estimated thickness for the location.

15 Claims, 8 Drawing Sheets

(56) References Cited

U.S. PATENT DOCUMENTS

| | | | |
|---|---|---|---|
| 9,002,088 B2* | 4/2015 | Ferguson | G01N 15/088 378/4 |
| 9,038,470 B1* | 5/2015 | Engelbart | G01N 29/04 73/599 |
| 2007/0006651 A1 | 1/2007 | Kruger et al. | |
| 2007/0119256 A1* | 5/2007 | Vaccaro | G01N 29/30 73/649 |
| 2012/0250970 A1* | 10/2012 | Tsubaki | G01N 29/0654 382/131 |

OTHER PUBLICATIONS

International Search Report and Written Opinion, dated Aug. 4, 2014, regarding Application No. PCT/US2014/034637, 10 pages.

Hsu et al., "Simultaneous ultrasonic velocity and sample thickness measurement and application in composites," The Journal of the Acoustical Society of America, vol. 92, No. 2, Aug. 1992, pp. 669-675.

Office Action, dated Oct. 24, 2014, regarding U.S. Appl. No. 13/568,985, 22 pages.

\* cited by examiner

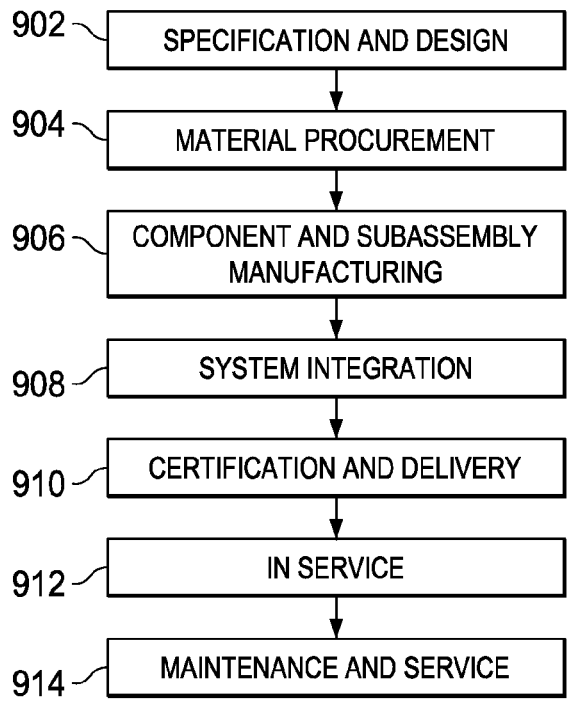
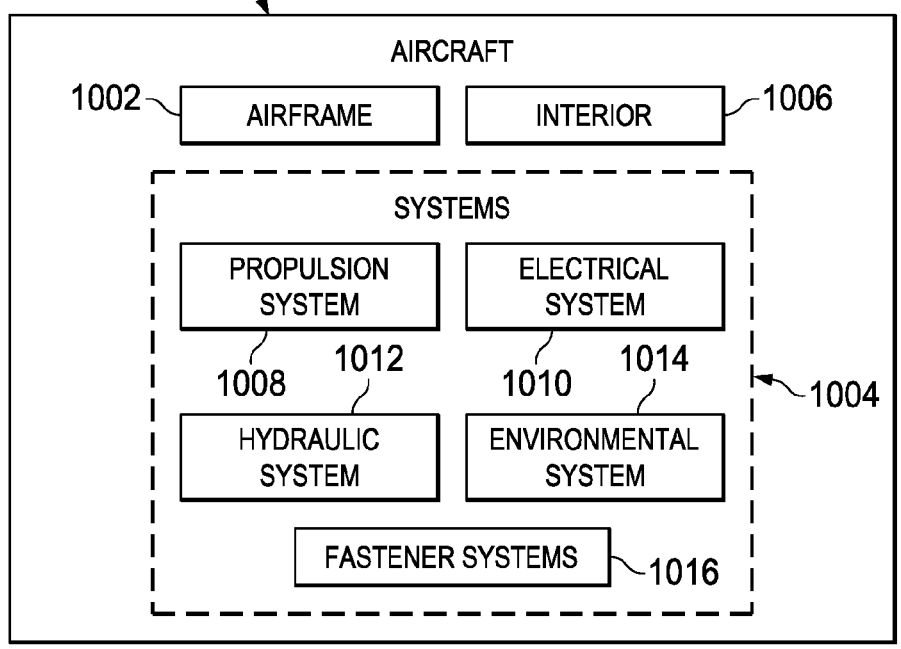

POROSITY INSPECTION SYSTEM FOR COMPOSITE STRUCTURE WITH NON-PARALLEL SURFACES

BACKGROUND INFORMATION

1. Field

The present disclosure relates generally to composite structures and, in particular, to inspecting composite structures. Still more particularly, the present disclosure relates to a method and apparatus for inspecting composite structures to identify porosity in the composite structures.

2. Background

Aircraft are being designed and manufactured with greater and greater percentages of composite materials. Composite materials are used in aircraft to decrease the weight of the aircraft. This decreased weight improves performance features such as payload capacity and fuel efficiency. Further, composite materials provide longer service life for various components in an aircraft.

Composite materials may be tough, light-weight materials created by combining two or more functional components. For example, a composite material may include reinforcing fibers bound in a polymer resin matrix. The fibers may be unidirectional or may take the form of a woven cloth or fabric. The fibers and resins may be arranged and cured to form a composite structure.

Using composite materials to create aerospace composite structures may allow for portions of an aircraft to be manufactured in larger pieces or sections. For example, a fuselage in an aircraft may be created in cylindrical sections to form the fuselage of the aircraft. Other examples include, without limitation, wing sections joined to form a wing or stabilizer sections joined to form a stabilizer.

In manufacturing composite structures, layers of composite material may be laid up on a tool. The layers of composite material may be comprised of fibers in sheets. These sheets may take the form of, for example, without limitation, fabrics, tape, tows, or other suitable configurations for the sheets. In some cases, resin may be infused or pre-impregnated into the sheets. These types of sheets are commonly referred to as prepreg.

The different layers of prepreg may be laid up in different orientations and different numbers of layers may be used depending on the desired thickness of the composite structure being manufactured. These layers may be laid up by hand or by using automated lamination equipment such as a tape laminating machine or a fiber placement system.

After the different layers have been laid up on the tool, the layers may be consolidated and cured upon exposure to temperature and pressure, thus forming the final composite structure. Thereafter, the composite structure may be inspected to ensure that inconsistencies are not present. The inspection may be performed using ultrasound testing, infrared testing, visual inspections, and other suitable types of testing.

This testing may be performed to identify various potential inconsistencies in the composite structure. For example, inconsistencies may include delamination, voids, undesired levels of porosity, and other types of inconsistencies.

With respect to porosity levels, increasing porosity in a composite structure may result in a less than desired load that the composite structure is able to withstand and perform as desired. Thus, a composite structure may be inspected using ultrasound testing to ensure that the porosity level is within a desired level for the composite structure.

Currently, when ultrasound testing is used to determine the porosity of the composite structure, the entire surface of the composite structure may be inspected. For example, an ultrasound system may perform ultrasound testing to gather data from all of the surfaces of each composite structure. This data may then be analyzed by an operator to identify the porosity of the composite structure. This inspection of the entire surface of the composite structure may take more time and manpower than desired.

Further, the analysis of the data of cross-sections with non-parallel surfaces may add to the time and manpower needed to inspect these composite structures. As a result, ultrasound testing of composite structures may take more time and may cost more than desired. Therefore, it would be desirable to have a method and apparatus that take into account at least some of the issues discussed above, as well as possibly other issues.

SUMMARY

In an illustrative embodiment, a method is provided. A thickness profile of a portion of a region of a composite structure is identified. The region has a cross-section with non-parallel surfaces. An estimated thickness for a location within the region and outside of the portion is identified using the thickness profile. An indication of whether the location has undesirable porosity is generated based on information about attenuation of response sound signals and the estimated thickness for the location.

In another illustrative embodiment, a method for inspecting a composite structure is provided. Information about attenuation of response sound signals in the composite structure is identified. An estimated thickness for a location in a region in the composite structure is identified from a thickness profile of the region. The region has a cross-section with non-parallel surfaces. A porosity of the composite structure at the location is identified based on the estimated thickness for the location and the information about the attenuation of the response sound signals at the location in the composite structure.

In a further illustrative embodiment, an ultrasound inspection system for a composite structure is provided. A number of transducers are configured to send sound signals into the composite structure and detect response sound signals to the sound signals sent into the composite structure. An analyzer is in communication with the number of transducers. The analyzer is configured to identify a thickness profile of a portion of a region of the composite structure, the region having a cross-section with non-parallel surfaces. The analyzer is further configured to identify an estimated thickness for a location within the region and outside of the portion using the thickness profile. The analyzer is still further configured to generate an indication of whether the location has undesirable porosity using the estimated thickness for the location and information about attenuation of the response sound signals detected by the number of transducers.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 9 is an illustration of an aircraft manufacturing and service method in the form of a block diagram in accordance with an illustrative embodiment; and FIG. 10 is an illustration of an aircraft in the form of a block diagram in which an illustrative embodiment may be implemented.

DETAILED DESCRIPTION

Figure 1:
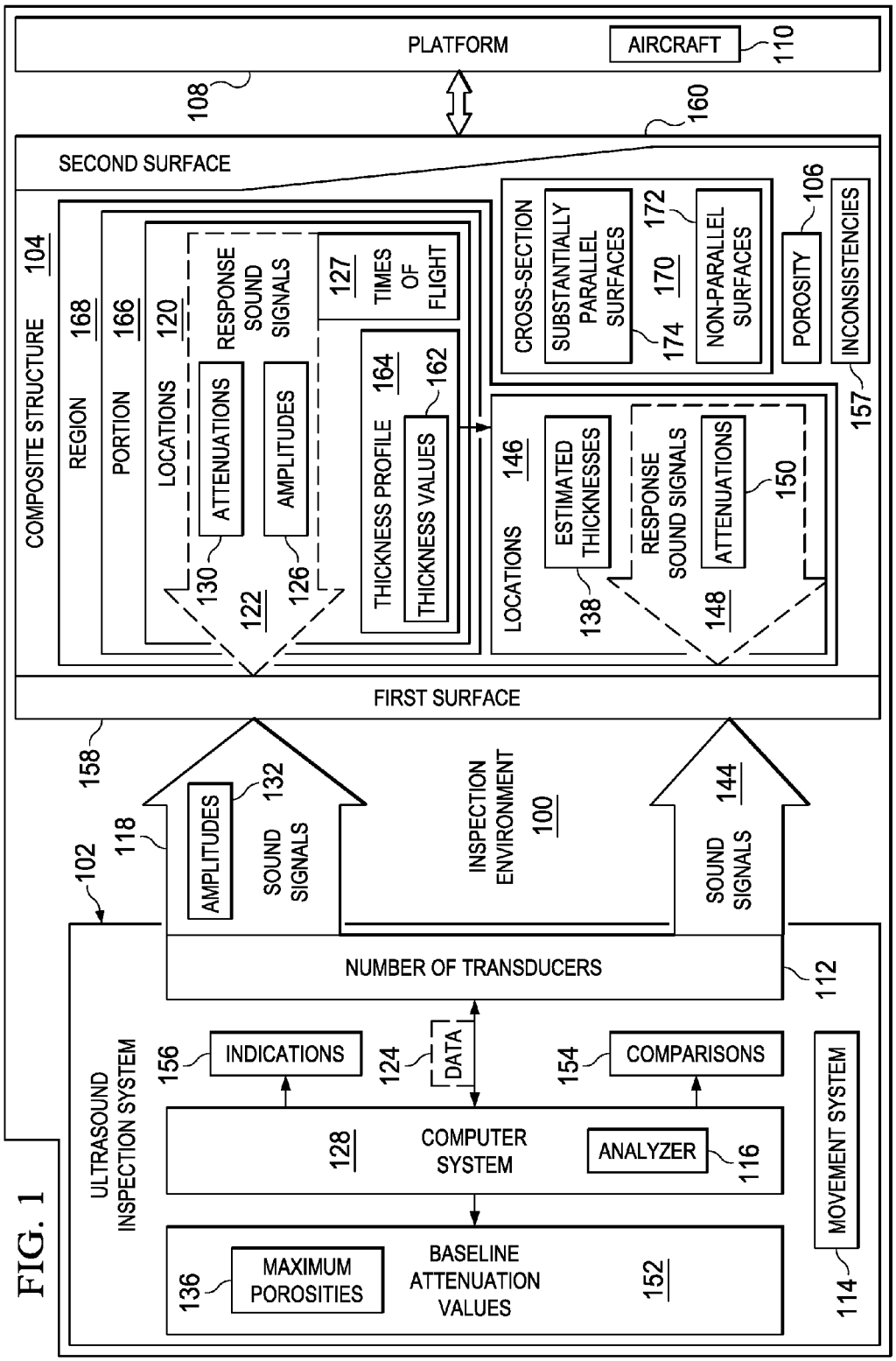
FIG. 1 is an illustration of a block diagram of an inspection environment in accordance with an illustrative embodiment.

The different illustrative embodiments recognize and take into account different considerations. For example, the different illustrative embodiments recognize and take into account that evaluating the level of porosity in a composite structure may be the most time-consuming aspect of an inspection. The illustrative embodiments recognize and take into account that a manufacturing rate may be improved by reducing the inspection time.

Further, the different illustrative embodiments recognize and take into account that composite structures having a cross-section with non-parallel surfaces may have increased inspection times. The different illustrative embodiments recognize and take into account that locations within composite structures may be returned as a "no-test." To evaluate porosity of a location of a composite structure, a thickness at the location is used. An area may be returned as "no-test" due to a thickness which cannot be determined from a response signal to sound signals sent into the composite structure. "No-test" locations may be automatically rejected.

Further, an operator may spend additional time during an analysis compensating for "no-test" locations. Yet further, "no-test" locations may require further analysis. This additional analysis may be more time-consuming and tedious than desired. Consequently, the manufacturing and testing of composite structures may be more expensive and less efficient than desired.

The different illustrative embodiments recognize and take into account that an area of composite structures having a cross-section with non-parallel surfaces may be inspected using a designated thickness. Each location in the area having the cross-section with non-parallel surfaces may be inspected using this same designated thickness.

The designated thickness may be a smallest thickness prior to the cross-section with non-parallel surfaces. The designated thickness may instead be a smallest estimated thickness of the cross-section with non-parallel surfaces. The designated thickness may be smaller than any thickness within the area having the cross-section with non-parallel surfaces.

The different illustrative embodiments recognize and take into account that by using a smaller thickness than an actual thickness at a location, the allowed porosity evaluation at the location may be more stringent than necessary. By using a designated thickness, a more stringent porosity evaluation than necessary may be applied to locations within the area having the non-parallel surfaces. As a result, composite structures having a cross-section with non-parallel surfaces may have a greater percentage of rejected material. Further, using a more stringent porosity evaluation may result in rejecting composite structure which is of acceptable porosity.

Thus, in one illustrative embodiment, a thickness profile of a portion of a region of a composite structure is identified. The region has a cross-section with non-parallel surfaces. An estimated thickness for a location within the region and outside of the portion is identified using the thickness profile. An indication of whether the location has undesirable porosity is generated based on information about attenuation of response sound signals and the estimated thickness for the location.

With reference now to the figures and, in particular, with reference to FIG. 1, an illustration of a block diagram of an inspection environment is depicted in accordance with an illustrative embodiment. In this depicted example, inspection environment 100 includes ultrasound inspection system 102. Ultrasound inspection system 102 may be used to perform an inspection of composite structure 104. In particular, an inspection may be conducted to determine porosity 106 in composite structure 104.

In this illustrative example, composite structure 104 may be part of platform 108. As depicted, platform 108 may take a number of different forms. In particular, platform 108 may take the form of aircraft 110. Composite structure 104 in aircraft 110 may be, for example, without limitation, one of a skin panel, a fuselage barrel, a stringer, a panel, a flap, a door, a wing box, or some other suitable type of composite structure.

Composite structure 104 may have first surface 158 and second surface 160. As depicted, first surface 158 and second surface 160 are substantially parallel to each other in some of composite structure 104 and first surface 158 and second surface 160 are non-parallel in some of composite structure 104. As a result, cross section 170 of composite structure 104 has non-parallel surfaces 172 and substantially parallel surfaces 174.

As depicted, ultrasound inspection system 102 may be comprised of number of transducers 112, movement system 114, analyzer 116, and other suitable components. Of course, ultrasound inspection system 102 may include other components not show in this depicted example.

In this illustrative example, number of transducers 112 may be configured to send sound signals 118 into composite structure 104 at locations 120. A "number of," as used herein with reference to items, means one or more items. For example, number of transducers 112 may be one or more transducers.

Locations 120 may form portion 166 of region 168 of composite structure 104 selected for inspection. In other words, region 168 of composite structure 104 may be selected for inspection. To begin inspection of region 168, number of transducers 112 may send sound signals 118 into locations 120 which form portion 166. Portion 166 may be a fraction of region 168 or may be all of region 168. In one illustrative example, portion 166 may have non-parallel surfaces 172, substantially parallel surfaces 174, or a combination thereof.

In some illustrative examples, portion 166 of region 168 may have a desirable reflection of sound signals 118 from second surface 160 of composite structure 104.

Sound signals 118 may be generated by number of transducers 112 under the control of analyzer 116 in this illustrative example. Sound signals 118 may have different frequencies. As depicted, sound signals 118 may be, for example, ultrasound signals. Without limitation, sound signals 118 may have a frequency from about 20 kilohertz to about 200 megahertz. Of course, other frequencies may be used for sound signals 118 depending on the particular implementation.

In response to sound signals 118 traveling into composite structure 104 at locations 120, response sound signals 122 may be generated. In this illustrative example, response sound signals 122 may be detected by number of transducers 112. In response to detecting response sound signals 122, number of transducers 112 may generate and send data 124 to analyzer 116 for processing. In some illustrative examples, data 124 may be, for example, electrical signals indicating amplitudes 126 of response sound signals 122. The electrical signals may be analog, digital, or some combination thereof. In some illustrative examples, data 124 may be, for example, electrical signals indicating times of flight 127 of response sound signals 122. Times of flight 127 may be periods of time from when sound signals 118 are sent into locations 120 and response sound signals 122 are detected by number of transducers 112.

In this illustrative example, analyzer 116 may be implemented using hardware, software, or a combination of the two. When software is used, the operations performed by analyzer 116 may be implemented in program code configured to be run on a processor unit. When hardware is employed, the hardware may include circuits that operate to perform operations in analyzer 116.

The hardware may take the form of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

In this illustrative example, analyzer 116 may be implemented in computer system 128. Computer system 128 may be one or more computers. When more than computer is present in computer system 128, those computers may be in communication with each other via a communication medium such as a network.

In this illustrative example, analyzer 116 may identify thickness values using ultrasound inspection of portion 166. Specifically, in this illustrative example, analyzer 116 may identify thickness values 162 for locations 120 from times of flight 127. Thickness values 162 may be thickness measurements at each location in locations 120. Thickness values 162 may form thickness profile 164 for locations 120 within portion 166. In some illustrative examples, portion 166 may comprise a line extending parallel to a direction of thickness variation in region 168. In these illustrative examples, thickness profile 164 may comprise thickness values for each location in locations 120 along the line comprising portion 166.

Thickness profile 164 may be applied to region 168. Thickness profile 164 may be applied to region 168 in a direction perpendicular to a direction of thickness variation in region 168. In other words, thickness profile 164 may be applied to region 168 in a direction perpendicular to a direction of variation of second surface 160.

Estimated thicknesses 138 of locations 146 within region 168 but outside of portion 166 may be identified by applying thickness profile 164 to region 168. Estimated thicknesses 138 may correspond to values in thickness values 162.

In this illustrative example, analyzer 116 may identify attenuations 130 of response sound signals 122. Attenuations 130 may be identified by comparing amplitudes 126 of response sound signals 122 with amplitudes 132 of sound signals 118.

Analyzer 116 may compare attenuations 130 with baseline attenuation values 152 to identify if porosity 106 in composite structure 104 at locations 120 is undesirable. Baseline attenuation values 152 represent maximum porosities 136 that are desired for thickness values 162 of composite structure 104 at locations 120.

In this illustrative example, thickness values 162 may be representative of distances from first surface 158 to second surface 160 at locations 120. Locations 120 where sound signals 118 enter composite structure 104 may be located on first surface 158. Second surface 160 may be substantially opposite to first surface 158. In these illustrative examples, baseline attenuation values 152 may be identified in a number of different ways.

For example, baseline attenuation values 152 may be baseline values taken for thicknesses of a test object that may be a reference standard, a requirements value, a value from a database, or some other suitable type of value for baseline attenuation values 152. As depicted, baseline attenuation values 152 may be threshold values.

Comparing attenuations 130 of response sound signals 122 to baseline attenuation values 152 may result in comparisons 154. If an attenuation in attenuations 130 is greater than the baseline attenuation value in baseline attenuation values 152 for a location in locations 120, then porosity 106 at the location in locations 120 may be greater than desired. As a result, additional evaluation of the location in locations 120 may be needed.

In this illustrative example, indications 156 may be generated by analyzer 116. Indications 156 may be generated based on comparisons 154 of attenuations 130 in response sound signals 122 and baseline attenuation values 152 for porosity 106 for thickness values 162 of locations 120 of composite structure 104.

Indications 156 may indicate whether additional evaluation of composite structure 104 may be needed at locations 120. Indications 156 may indicate that additional evaluation of composite structure 104 may be needed at locations 120 or that additional evaluation of composite structure 104 may not be needed at locations 120.

Further, analyzer 116 may control number of transducers 112 to send sound signals 144 into locations 146 in composite structure 104. As depicted, analyzer 116 may control movement system 114 to move number of transducers 112 with respect to composite structure 104 to locations 146 on at least one of first surface 158 and second surface 160. Number of transducers 112 may then send sound signals 144 into locations 146 of region 168 on composite structure 104. In this manner, ultrasound inspection system 102 may test all of region 168 of composite structure 104.

In response to sound signals 144 being sent into locations 146, response sound signals 148 may be generated. Number of transducers 112 may detect response sound signals 148 and generate data 124 about response sound signals 148.

Analyzer 116 may receive data 124 about response sound signals 148 from number of transducers 112 and identify attenuations 150 for response sound signals 148. Analyzer 116 may compare attenuations 150 with baseline attenuation values 152 to identify if porosity 106 in composite structure 104 at locations 146 is undesirable. As each estimated thickness in estimated thicknesses 138 corresponds to a thickness value in thickness values 162, baseline attenuation values 152 represent maximum porosities 136 that are desired for estimated thicknesses 138 of composite structure 104 at locations 146. In this illustrative example, a baseline attenuation value in baseline attenuation values 152 is selected for each location in locations 146 based on a corresponding estimated thickness in estimated thicknesses 138. In comparing attenuations 150 with baseline attenuation values 152, analyzer 116 forms comparisons 154. Based on comparisons 154 of attenuations 150 with baseline attenuation values 152, analyzer 116 may generate indications 156. Indications 156 may indicate that porosity 106 at locations 146 is undesirable. If porosity 106 at a location in locations 146 is undesirable, this may be an inconsistency in inconsistencies 157. Accordingly, an area having inconsistencies in inconsistencies 157 within region 168 of composite structure 104 may be identified based on attenuations 150 of response sound signals 148 and thickness profile 164.

Indications 156 may indicate whether additional evaluations of locations 146 are needed at locations 146. These additional evaluations may be additional evaluations for areas of composite structure 104 that may show disbonding or delamination. When disbonding and/or delamination may be present, indications 156 may show heavier levels of porosity than desired. In this illustrative example, these areas of porosity, indicated by indications 156, may be retested.

In other illustrative examples, additional ultrasound testing may be performed on composite structure 104 using a different transducer in number of transducers 112 than was used to send sound signals 118 into composite structure 104 during the first test. Further, areas of composite structure 104 may be retested using a different frequency from number of transducers 112. In this manner, ultrasound inspection system 102 and/or other types of inspection systems may be used to further inspect areas of composite structure 104.

Thus, the illustrative embodiments provide a method to identify the porosity of composite structure 104 using ultrasound inspection system 102. With the comparison of attenuations 130 to response sound signals 122 and baseline attenuation values 152, an operator may use the illustrative embodiments to quickly and efficiently determine porosity 106 within region 168 of composite structure 104.

The illustration of inspection environment 100 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, in some illustrative examples, comparisons 154 may not be created based on response sound signals 122. In these illustrative examples, thickness values 162 may be identified based on response sound signals 122. However, comparisons 154 may be created based on a second set of response sound signals in response to a second set of sound signals sent into locations 120.

As another illustrative example, thickness values 162 may not be identified based on times of flight 127 of response sound signals 122. Thickness values 162 may instead be identified based on thicknesses of corresponding locations in a model of composite structure 104.

Figure 2:
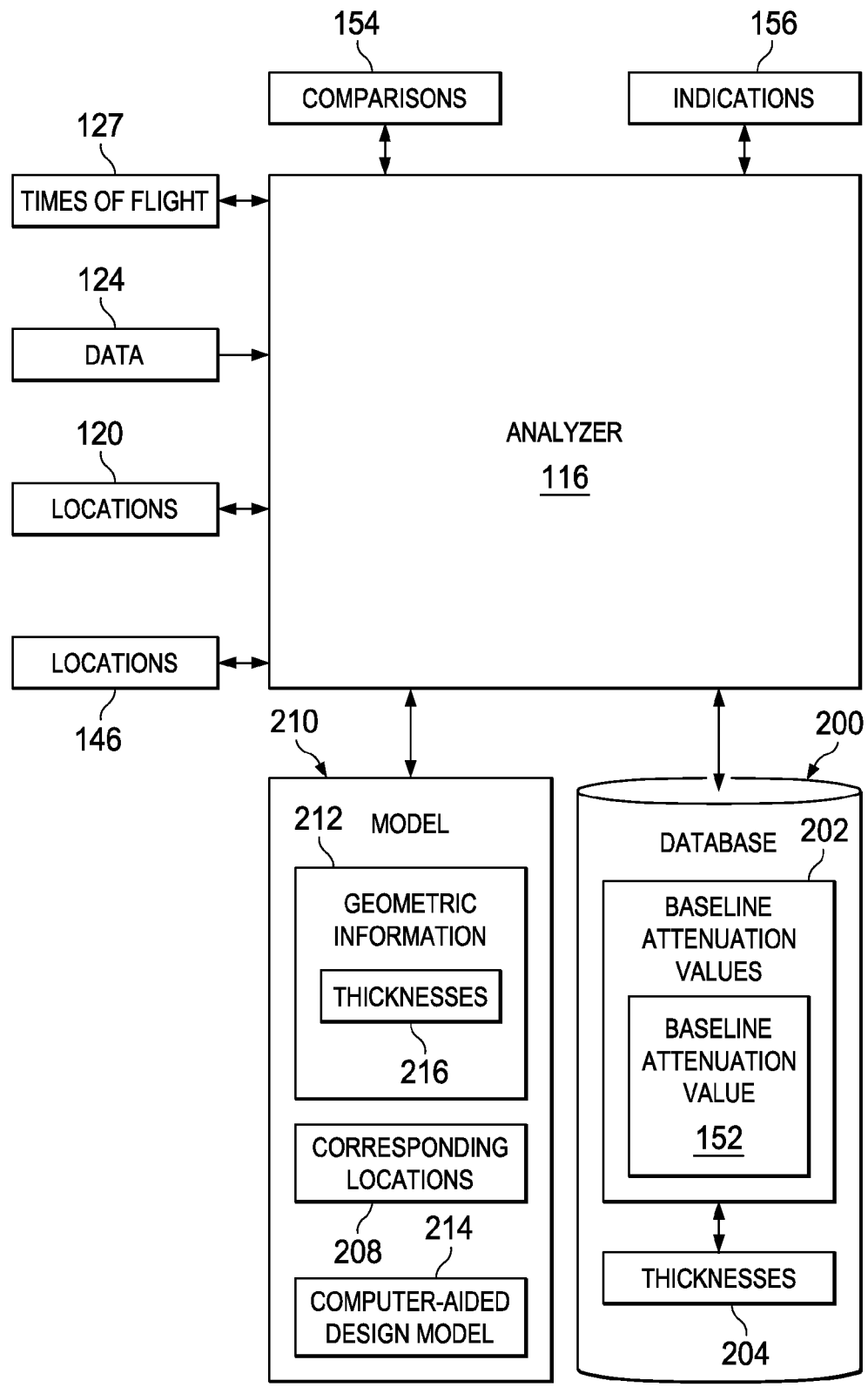
FIG. 2 is an illustration of data flow in an analysis of data for response sound signals in accordance with an illustrative embodiment.

Turning now to FIG. 2, an illustration of data flow in an analysis of data for response sound signals is depicted in accordance with an illustrative embodiment. As depicted, analyzer 116 receives data 124 about response sound signals 122 and response sound signals 148 generated in response to sound signals 118 and sound signals 144 being sent into composite structure 104 at locations 120 and locations 146 as shown in FIG. 1. Data 124 may be used to identify attenuations 130 and attenuations 150 in response sound signals 122 and response sound signals 148 as shown in FIG. 1.

With attenuations 130, database 200 may be used to identify baseline attenuation values 152 from baseline attenuation values 202. In these illustrative examples, baseline attenuation values 202 may be indexed in a number of different ways. For example, thicknesses 204 may be used as an index in baseline attenuation values 202. Thicknesses 204 may correspond to thicknesses in composite structure 104 in FIG. 1.

In one illustrative example, analyzer 116 may use thickness values 162 of composite structure 104 at locations 120 as shown in FIG. 1 as an index to identify baseline attenuation values 152 that correspond to thickness values 162 in thicknesses 204 in database 200. In other words, thicknesses 204 serves as an index to identify baseline attenuation values 152 for thickness values 162 at locations 120.

Thickness values 162 may be identified in a number of different ways. For example, locations 120 may be used to identify corresponding locations 208 in model 210 from which an estimate of thickness values 162 may be identified using geometric information 212 in model 210.

In this illustrative example, model 210 may be a model of composite structure 104. As another example, model 210 may be a model of platform 108 including composite structure 104 as shown in FIG. 1. In this illustrative example, model 210 takes the form of computer-aided design (CAD) model 214.

As depicted, geometric information 212 may be, for example, without limitation, thicknesses, lengths, orientations, or other information regarding features of composite structure 104. Corresponding locations 208 in model 210 may correspond to locations 120 on composite structure 104. In other words, corresponding locations 208 may be representations of locations 120 on composite structure 104 in model 210.

With corresponding locations 208 in model 210, analyzer 116 may identify thicknesses 216 for corresponding locations 208 from geometric information 212 for composite structure 104 in model 210. However, thicknesses 216 may only be estimates of thickness values 162 for composite structure 104 at locations 120. Variances may occur in thickness values 162 relative to thicknesses 216 during manufacturing of composite structure 104. Depending on the implementation, thicknesses 216 may be sufficiently accurate for use by analyzer 116.

In another illustrative example, analyzer 116 may identify thickness values 162 without using model 210. For example, without limitation, thicknesses 204 may be identified based on times of flight 127. Times of flight 127 may be periods of time from when sound signals 118 are sent into locations 120 and response sound signals 122 are detected in FIG. 1.

With times of flight 127, analyzer 116 may identify thickness values 162 using other parameters of sound signals 118. For example, the speed of sound signals 118 may be used in determining thicknesses 204 when times of flight 127 are used.

After baseline attenuation values 152 are identified, analyzer 116 may then compare baseline attenuation values 152 with attenuations 130 and attenuations 150 to generate comparisons 154 in FIG. 1. In comparing baseline attenuation values 152 with attenuations 130, thickness values 162 are used. In comparing baseline attenuation values 152 with attenuations 150, estimated thicknesses 138 are used. With comparisons 154, indications 156 may be generated indicating whether additional evaluation of locations 120 and locations 146 is needed.

By applying thickness profile 164 to region 168, thickness evaluations need not be done for locations 146 in region 168. As a result, ultrasound testing on composite structure 104 may be conducted efficiently and with less time-consuming data analysis. Further, by using estimated thicknesses 138, locations 146 may not be labeled as "no-test" areas. Thus an operator may focus on areas of composite structure 104 that need additional evaluation and analysis instead of analyzing all data over the entire surface of composite structure 104 in FIG. 1.

Figure 3:
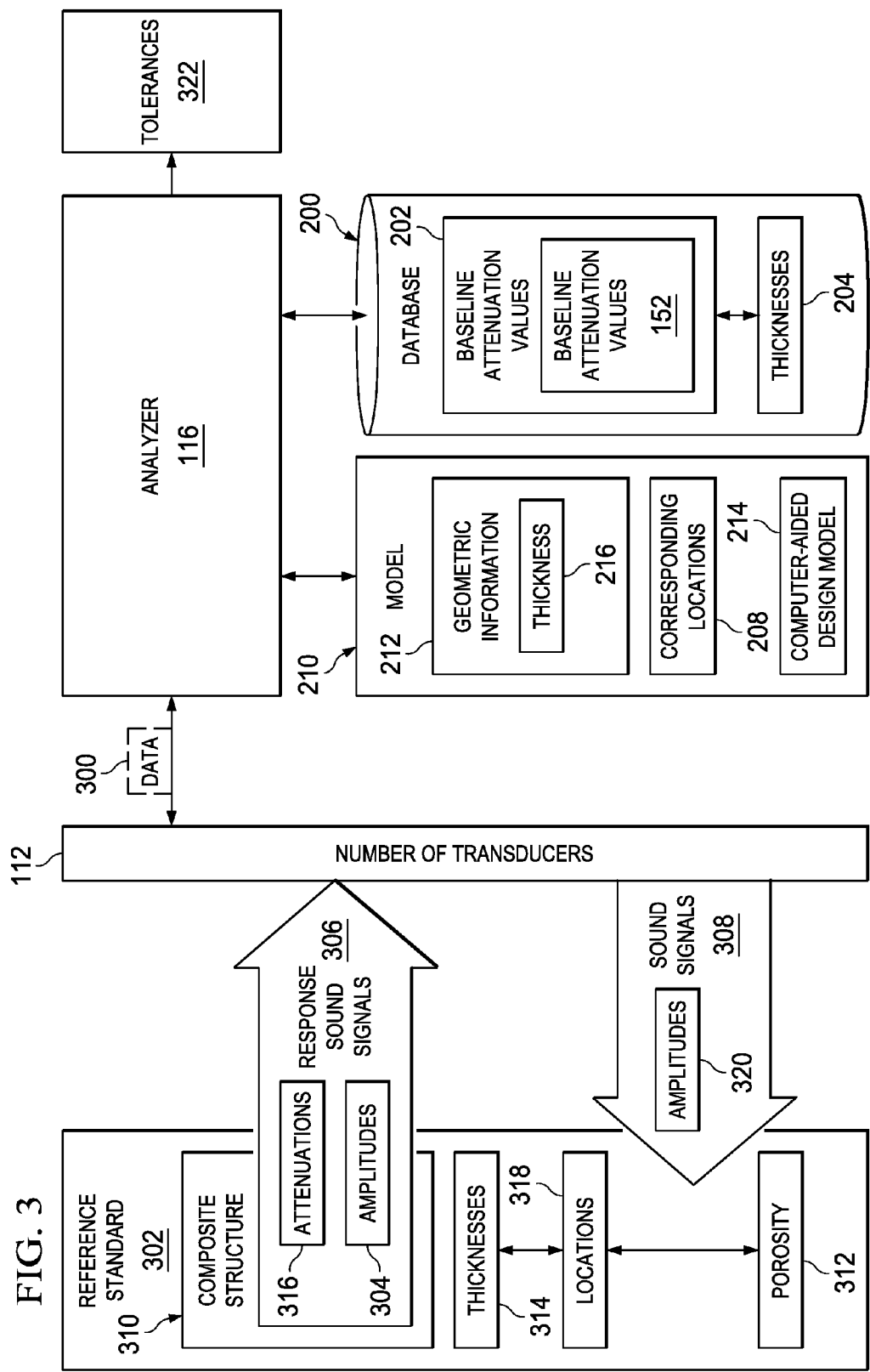
FIG. 3 is an illustration of data flow in creating baseline attenuation values in accordance with an illustrative embodiment.

Turning now to FIG. 3, an illustration of data flow in creating baseline attenuation values is depicted in accordance with an illustrative embodiment. This figure illustrates the generation of baseline attenuation values 202 for database 200.

In this illustrative example, analyzer 116 may receive data 300. Data 300 may be generated using reference standard 302. In particular, data 300 may include amplitudes 304 of response sound signals 306 generated in response to sending sound signals 308 into reference standard 302 using number of transducers 112.

Reference standard 302 may be composite structure 310. As depicted, reference standard 302 may have the same or different dimensions as composite structure 104 in FIG. 1. Reference standard 302 has porosity 312 at a desired level throughout composite structure 310 for thicknesses 314.

With amplitudes 304 in data 300, attenuations 316 in response sound signals 306 may be identified for reference standard 302 for locations 318 in reference standard 302. For example, attenuations 316 may be identified by comparing amplitudes 304 in response sound signals 306 with amplitudes 320 for sound signals 308.

In particular, attenuations 316 may be values for thicknesses 314 at locations 318 in reference standard 302. Attenuations 316 may represent values for porosity 312 in reference standard 302.

Additionally, analyzer 116 may identify tolerances 322 for porosity 312. Tolerances 322 may be based on a number of different factors. For example, tolerances 322 may be based on at least one of a desired load for reference standard 302, safety margins, and other suitable factors. With tolerances 322, attenuations 316 may be adjusted to obtain baseline attenuation values 202.

In these illustrative examples, tolerances 322 may be an allowable adjustment in porosity 312 for reference standard 302. Tolerances 322 may be the same for locations 318 or may be different for different locations in locations 318. This adjustment may be an increase in porosity 312. This adjustment may be made by increasing attenuations 316 that reflect the increase in porosity 312 that may be allowable.

As depicted, baseline attenuation values 202 in database 200 may take a number of different forms. For example, without limitation, baseline attenuation values 202 may take the form of graphs of curves, tables, length lists, flat files, and other suitable forms.

In this manner, ultrasound inspection of reference standard 302 may provide baseline attenuation values 202 for use in ultrasound inspection of composite structure 104 in FIG. 1. Further, acceptable tolerances for porosity 106 in composite structure 104 may be identified. With the identification of tolerances 322, database 200 of baseline attenuation values 202 may be generated for different thicknesses in thicknesses 204 of composite structure 104 and used for inspecting composite structure 104 in FIG. 1.

The illustrations of data flows in FIGS. 2 and 3 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, baseline attenuation values 202 may be indexed to locations in database 200. The locations in database 200 may correspond to locations in composite structure 104 in FIG. 1.

Figure 4:
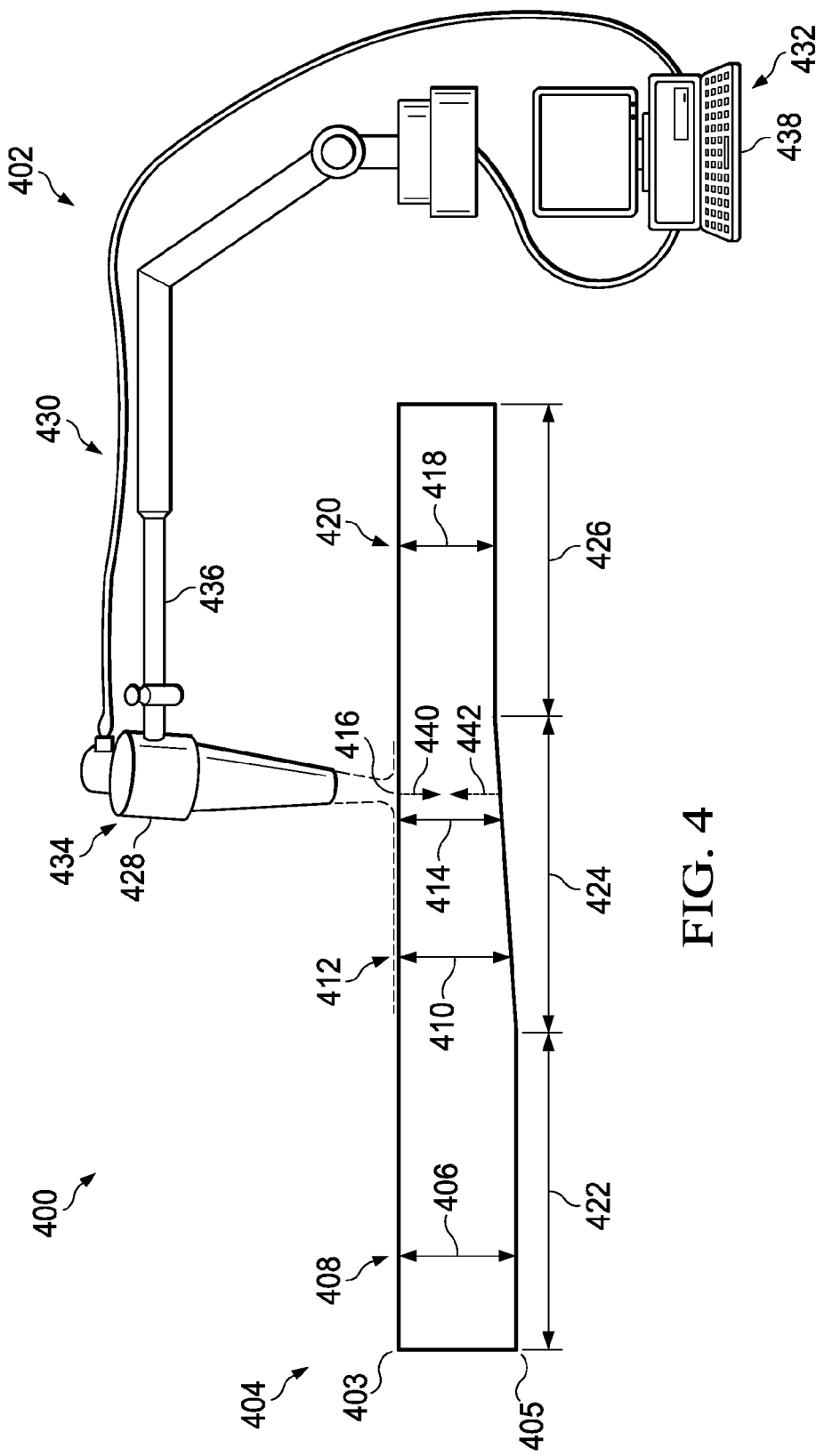
FIG. 4 is an illustration of an inspection environment in accordance with an illustrative embodiment.

Turning now to FIG. 4, an illustration of an inspection environment is depicted in accordance with an illustrative embodiment. In this depicted example, inspection environment 400 is an example of a physical implementation for inspection environment 100 and components in inspection environment 100 in FIG. 1 and FIG. 2.

In this illustrative example, inspection environment 400 includes ultrasound inspection system 402, which may be configured to inspect composite structure 404. Composite structure 404 has first surface 403 and second surface 405. As can be seen in this illustrative example, composite structure 404 may have thickness 406 at location 408, thickness 410 at location 412, thickness 414 at location 416, and thickness 418 at location 420. As can be seen, thickness 406, thickness 410, thickness 414, and 418 are each different in composite structure 404.

Thickness 406 is located in parallel surface area 422. Thicknesses within parallel surface area 422 are substantially the same as thickness 406. Thickness 410 and thickness 414 are located in non-parallel surface area 424. Thicknesses within non-parallel surface area 424 vary. As depicted, second surface 405 angles upward at a substantially constant angle. In some other illustrative examples, second surface 405 may instead angle upward at a varying angle. In some other illustrative examples, second surface 405 may angle downwards in a constant or varying angle. In yet other illustrative examples, second surface 405 may be a combination of upward and downward angles. Thickness 418 is located in parallel surface area 426. Thicknesses within parallel surface area 426 are substantially the same as thickness 418.

In this depicted example, ultrasound inspection system 402 may include number of transducers 434, movement system 430, and analyzer 432. As depicted, number of transducers 434 may include transducer 428. Transducer 428 may be configured to be moved by movement system 430.

In this example, movement system 430 may include robotic arm 436. Robotic arm 436 may be configured to be controlled by analyzer 432. In this illustrative example, robotic arm 436 may be configured to move transducer 428 to different locations on first surface 403 of composite structure 404.

In this illustrative example, transducer 428 may be configured to send sound signal 440 into composite structure 404 at location 416. Additionally, transducer 428 may also be configured to detect response sound signal 442. Transducer 428 generates data and sends the data to analyzer 432 in response to detecting response sound signal 442.

In this illustrative example, analyzer 432 may be implemented in computer 438. Computer 438 may be one implementation for a computer in computer system 128 shown in block form in FIG. 1. Analyzer 432 may identify the attenuation for response sound signal 442 and determine whether an indication should be generated for location 416. This determination may be based on a desired level of porosity for thickness 414 at location 416. The attenuation may be used to identify the amount of porosity based on thickness 414 at location 416.

In these illustrative examples, transducer 428 may be moved by robotic arm 436 to other locations on first surface 403 of composite structure 404 to send additional sound signals and detect additional response sound signals. This information from other locations may be used to generate indications of whether additional evaluation is needed for those locations.

Figure 5:
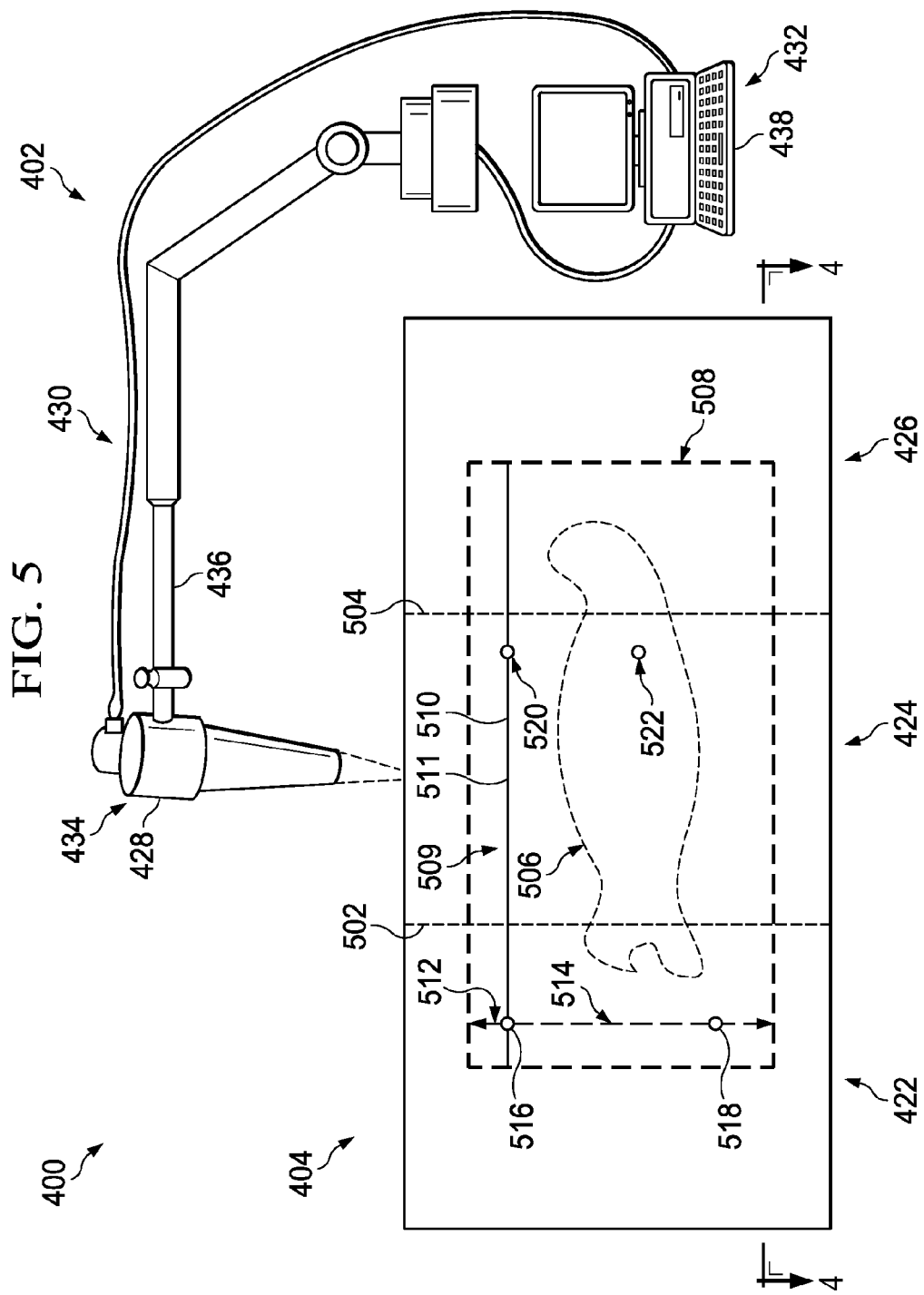
FIG. 5 is another illustration of an inspection environment in accordance with an illustrative embodiment.

Turning now to FIG. 5, another illustration of an inspection environment is depicted in accordance with an illustrative embodiment. In this depicted example, inspection environment 400 is an example of a physical implementation for inspection environment 100 and components in inspection environment 100 in FIG. 1 and FIG. 2. FIG. 5 is a depiction of inspection environment 400. In this illustrative example, FIG. 4 is a view of FIG. 5 along cross-section line 4.

In this illustrative example, inspection environment 400 includes ultrasound inspection system 402 which may be configured to inspect composite structure 404. Composite structure 404 has parallel surface area 422, non-parallel surface area 424, and parallel surface area 426. Parallel surface area 422 and non-parallel surface area 424 are separated by line 502. Line 502 may represent the beginning of an angle in second surface 405 of composite structure 404. Non-parallel surface area 424 and parallel surface area 426 are separated by line 504. Line 504 may represent the end of an angle in second surface 405 of composite structure 404. Composite structure 404 may have area of undesirable porosity 506. Area of undesirable porosity 506 may be identified by inspecting composite structure 404 using ultrasound inspection system 402.

In this illustrative example, ultrasound inspection system 402 may be configured to inspect region 508 of composite structure 404. Region 508 may be identified for inspection by a human operator or by computer 438. To inspect region 508 of composite structure 404, ultrasound inspection system 402 may send signals into locations within region 508. Attenuations of response sound signals received from locations within region 508 may be used to identify porosity of region 508.

To determine porosity of a location in region 508, attenuation for the location may be compared to a baseline attenuation for a thickness of the location. Region 508 has portion 510. As depicted, portion 510 is a line extending across region 508. In some illustrative examples, portion 510 may instead be an area, a point, or other suitable section of region 508.

In this illustrative example, thicknesses for locations in region 508 may be identified by applying thickness profile 511 of portion 510 to region 508. Thickness values in thickness profile 511 may be identified in a variety of ways.

In one illustrative example, thickness values in thickness profile 511 may be identified using ultrasound inspection system 402. To identify thicknesses of locations in portion 510, ultrasound inspection system 402 may send sound signals such as sound signals 118 of FIG. 1 into locations 509 in portion 510. The thickness values for each location in locations 509 may be identified from times of flight such as times of flight 127 of FIG. 1 of response sound signals such as response sound signals 122 of FIG. 1 received from locations 509. The thickness values for portion 510 form thickness profile 511 of region 508.

In other illustrative examples, thickness values in thickness profile 511 may be identified from a model, such as model 210 of FIG. 2. In these illustrative examples, thicknesses for corresponding locations in the model may be applied to locations within portion 510. The thickness values for portion 510 form thickness profile 511 of region 508.

Thickness profile 511 may next be applied to region 508. In this illustrative example, thickness profile 511 is applied to region 508 in a direction perpendicular to the direction of thickness variation in region 508. In this illustrative example, thickness profile 511 is applied to region 508 in direction 512 and direction 514.

By applying thickness profile 511 to region 508, estimated thicknesses are identified for locations within region 508 that are outside of portion 510. For example, location 516 is within portion 510. Location 516 will have a thickness value within thickness profile 511. By applying thickness profile 511 along direction 514, the thickness value of location 516 will be applied to location 518. As a result, the estimated thickness of location 518 will be the same value or substantially the same value as the thickness value of location 516.

Likewise, location 520 of portion 510 will have a thickness value within thickness profile 511. By applying thickness profile 511 along direction 514, the thickness value of location 520 will be applied to location 522.

In one illustrative example, analyzer 432 may identify the attenuation for a response sound signal received from location 518. Analyzer 432 may determine whether an indication should be generated for location 518. This determination may be based on a desired level of porosity for the estimated thickness of location 518, which is equivalent to the thickness value of location 516.

In one illustrative example, analyzer 432 may identify the attenuation for a response sound signal received from location 522. Analyzer 432 may determine whether an indication should be generated for location 522. This determination may be based on a desired level of porosity for the estimated thickness of location 522, which is equivalent to the thickness value of location 520.

The different components illustrated for inspection environment 400 are not meant to provide architectural limitations to the manner in which different embodiments may be implemented. The different illustrative embodiments may be implemented in an inspection environment including components in addition to and/or in place of those illustrated for inspection environment 400. Other components shown in FIGS. 4 and 5 can be varied from the illustrative examples shown. For example, computer 438 may communicate with number of transducers 434 over a wireless connection.

The different components shown in FIGS. 4 and 5 may be combined with components in FIGS. 1-3, used with components in FIGS. 1-3, or a combination of the two. Additionally, some of the components in FIGS. 4 and 5 may be illustrative examples of how components shown in block form in FIGS. 1-3 can be implemented as physical structures.

Figure 6:
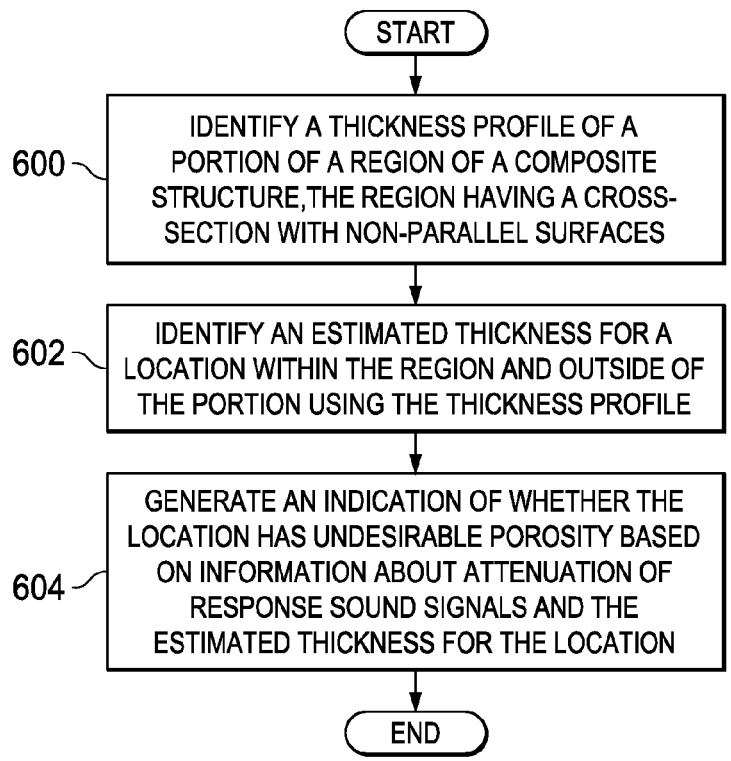
FIG. 6 is an illustration of a flowchart of a process for detecting porosity in composite structures in accordance with an illustrative embodiment.

Turning now to FIG. 6, an illustration of a flowchart of a process for detecting porosity in composite structures is depicted in accordance with an illustrative embodiment. The process illustrated in FIG. 6 may be implemented using ultrasound inspection system 102 in FIG. 1. Further, this process may be implemented to inspect composite structure 104 for porosity 106 in FIG. 1.

The process may begin by identifying a thickness profile of a portion of a region of a composite structure, the region having a cross-section with non-parallel surfaces (operation 600). The process may then identify an estimated thickness for a location within the region and outside of the portion using the thickness profile (operation 602). The process may then generate an indication of whether the location has undesirable porosity based on information about attenuation of response sound signals and the estimated thickness for the location (operation 604). Afterwards, the process terminates.

Figure 7:
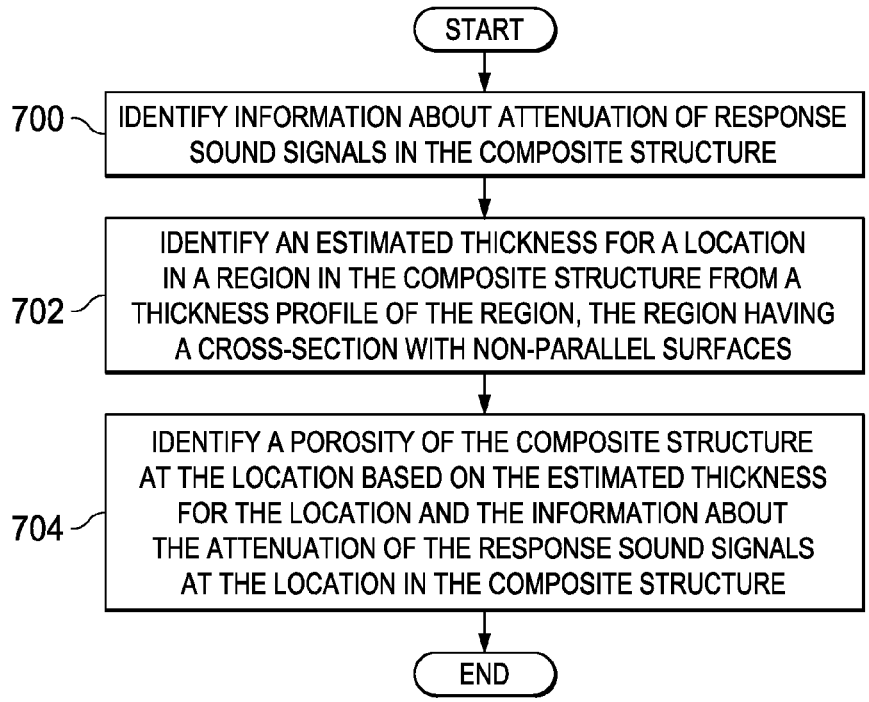
FIG. 7 is another illustration of a flowchart of a process for detecting porosity in composite structures in accordance with an illustrative embodiment.

Turning now to FIG. 7, another illustration of a flowchart of a process for detecting porosity in composite structures is depicted in accordance with an illustrative embodiment. The process illustrated in FIG. 7 may be implemented using ultrasound inspection system 102 in FIG. 1. Further, this process may be implemented to inspect composite structure 104 for porosity 106 in FIG. 1.

The process may begin by identifying information about attenuation of response sound signals in the composite structure (operation 700). The process may then identify an estimated thickness for a location in a region in the composite structure from a thickness profile of the region, the region having a cross-section with non-parallel surfaces (operation 702). The process may then identify a porosity of the composite structure at the location based on the estimated thickness for the location and the information about the attenuation of the response sound signals at the location in the composite structure (operation 704). Afterwards, the process terminates.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

For example, in FIG. 7, information about attenuation of response sound signals is identified. All of the response sound signals may be received in operation 700 before identifying attenuations for the response sound signals. This type of processing may be referred to as a post-processing of data. In some illustrative examples, the operations may be performed each time a response sound signal is received rather than after all of the response sound signals have been received. This type of processing may be referred to as dynamic processing of data.

Figure 8:
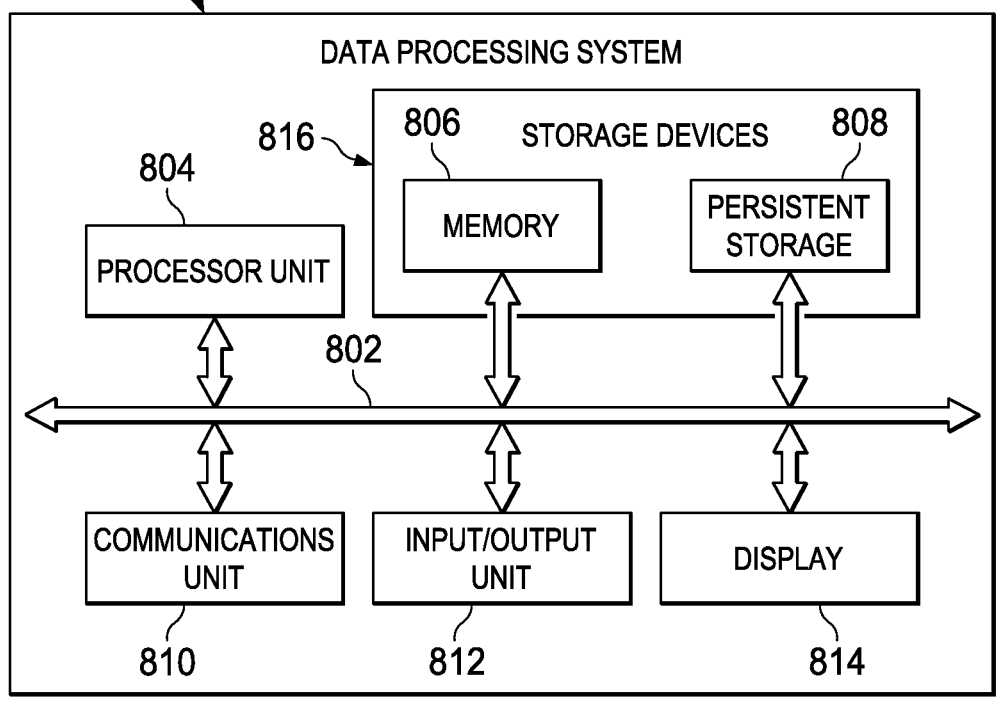
FIG. 8 is an illustration of a data processing system in the form of a block diagram in accordance with an illustrative embodiment.

Turning now to FIG. 8, an illustration of a data processing system is depicted in the form of a block diagram in accordance with an illustrative embodiment. Data processing system 800 may be used to implement one or more computers in computer system 128 in FIG. 1. In this illustrative example, data processing system 800 includes communications framework 802, which may provide communications between processor unit 804, memory 806, persistent storage 808, communications unit 810, input/output (I/O) unit 812, and display 814. In this example, communications framework 802 may take the form of a bus system.

Processor unit 804 may execute instructions for software that may be loaded into memory 806. Processor unit 804 may be a number of processors, a multi-processor core, or some other type of processor, depending on the particular implementation.

Memory 806 and persistent storage 808 may be examples of storage devices 816. A storage device may be any piece of hardware that is capable of storing information, such as, for example, without limitation, data, program code in functional form, and/or other suitable information either on a temporary basis and/or a permanent basis. Storage devices 816 may also be referred to as computer readable storage devices in these illustrative examples. Memory 806, in these examples, may be, for example, a random access memory or any other suitable volatile or non-volatile storage device. Persistent storage 808 may take various forms, depending on the particular implementation.

For example, persistent storage 808 may contain one or more components or devices. For example, persistent storage 808 may be a hard drive, a flash memory, a rewritable optical disk, a rewritable magnetic tape, or some combination of the above. The media used by persistent storage 808 also may be removable. For example, a removable hard drive may be used for persistent storage 808.

Communications unit 810, in these illustrative examples, may provide for communications with other data processing systems or devices. In these illustrative examples, communications unit 810 may be a network interface card.

Input/output (I/O) unit 812 may allow for input and output of data with other devices that may be connected to data processing system 800. For example, input/output (I/O) 812 may provide a connection for user input through a keyboard, a mouse, and/or some other suitable input device. Further, input/output (I/O) unit 812 may send output to a printer. Display 814 provides a mechanism to display information to a user.

Instructions for the operating system, applications, and/or programs may be located in storage devices 816, which are in communication with processor unit 804 through communications framework 802. The processes of the different embodiments may be performed by processor unit 804 using computer-implemented instructions, which may be located in a memory, such as memory 806.

These instructions may be referred to as program code, computer usable program code, or computer readable program code that may be read and executed by a processor in processor unit 804. The program code in the different embodiments may be embodied on different physical or computer readable storage media, such as memory 806 or persistent storage 808.

Program code 818 may be located in a functional form on computer readable media 820 that is selectively removable and may be loaded onto or transferred to data processing system 800 for execution by processor unit 804. Program code 818 and computer readable media 820 may form computer program product 822 in these illustrative examples. In one example, computer readable media 820 may be computer readable storage media 824 or computer readable signal media 826.

In these illustrative examples, computer readable storage media 824 is a physical or tangible storage device used to store program code 818 rather than a medium that propagates or transmits program code 818.

Alternatively, program code 818 may be transferred to data processing system 800 using computer readable signal media 826. Computer readable signal media 826 may be, for example, a propagated data signal containing program code 818. For example, computer readable signal media 826 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 800 are not meant to provide architectural limitations to the manner in which different embodiments may be implemented. The different illustrative embodiments may be implemented in a data processing system including components in addition to and/or in place of those illustrated for data processing system 800. Other components shown in FIG. 8 can be varied from the illustrative examples shown. The different embodiments may be implemented using any hardware device or system capable of running program code 818.

Illustrative embodiments of the disclosure may be described in the context of aircraft manufacturing and service method 900 as shown in FIG. 9 and aircraft 1000 as shown in FIG. 10. For example, ultrasound inspection system 102 in FIG. 1 may be used during at least one of the steps shown in this figure.

Turning first to FIG. 9, an illustration of an aircraft manufacturing and service method is depicted in the form of a block diagram in accordance with an illustrative embodiment. During pre-production, aircraft manufacturing and service method 900 may include specification and design 902 of aircraft 1000 in FIG. 10 and material procurement 904.

During production, component and subassembly manufacturing 906 and system integration 908 of aircraft 1000 in FIG. 10 takes place. Thereafter, aircraft 1000 in FIG. 10 may go through certification and delivery 910 in order to be placed in service 912. While in service 912 by a customer, aircraft 1000 in FIG. 10 is scheduled for routine maintenance and service 914, which may include modification, reconfiguration, refurbishment, and other maintenance or service.

Each of the processes of aircraft manufacturing and service method 900 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 10, an illustration of an aircraft is depicted in the form of a block diagram in which an illustrative embodiment may be implemented. Aircraft 1000 may be one implementation for platform 108 in FIG. 1. Specifically, aircraft 1000 may be one implementation for aircraft 110 in FIG. 1.

In this example, aircraft 1000 is produced by aircraft manufacturing and service method 900 in FIG. 9 and may include airframe 1002 with plurality of systems 1004 and interior 1006. Examples of systems 1004 include one or more of propulsion system 1008, electrical system 1010, hydraulic system 1012, and environmental system 1014. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 900 in FIG. 9. In one illustrative example, composite structures manufactured during component and subassembly manufacturing 906 may be inspected using ultrasound inspection system 102 in FIG. 1 as well as composite structures that may be manufactured while aircraft 1000 is in service 912 or during maintenance and service 914. One or more apparatus embodiments, method embodiments, or a combination thereof may be utilized while aircraft 1000 is in service 912 and/or during maintenance and service 914 in FIG. 9. The use of a number of the different illustrative embodiments may substantially expedite the assembly of and/or reduce the cost of aircraft 1000.

Thus, the illustrative embodiments provide a method and apparatus for inspecting composite structures. By using ultrasound inspection system 102, inspections of composite structures may be made more quickly and with less effort from operators. Ultrasound inspection system 102 is configured to provide indications of whether additional evaluations are needed by an operator. These indications may be based on a comparison of the attenuation in response sound signals to baseline attenuation values. These baseline attenuation values may be selected to provide an indication of when the porosity is greater than a desired level. Thus, when the attenuation is greater than a baseline attenuation value, additional evaluation of the location may be needed.

In inspecting the composite structure, thickness values may be identified for locations within a portion of a region being inspected. A thickness profile may comprise these thickness values. The thickness profile may be applied to the region. Accordingly, estimated thicknesses may be applied to locations within the region but outside of the portion. The estimated thicknesses may have the same or substantially the same values as the thickness values in the thickness profile. Baseline attenuation values for locations in the region but outside of the portion may be selected based on estimated thicknesses. Thus thicknesses for each location need not be individually identified.

By using estimated thicknesses for non-parallel areas, less stringent porosity requirements may be applied than using a single designated thickness. Accordingly, using estimated thicknesses for non-parallel areas may result in less rejected material. Further, by using estimated thicknesses for non-parallel areas, these areas may not be labelled as "non-test" areas. Thus, by using estimated thicknesses for non-parallel areas, operators may spend less time compensating for "no-test" regions.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:
1. A method comprising:
using a transducer to transmit ultrasonic waves into a portion of a region of a composite structure, the region having a cross-section with non-parallel surfaces;
identifying, using a processor, a thickness profile of the portion of the region of the composite structure, the thickness profile comprising a plurality of thickness measurements of the portion based on times of flight of the ultrasonic waves;

identifying, using a processor, an estimated thickness for a location within the region and outside of the portion using the thickness profile; and generating, using a processor, an indication of whether the location has undesirable porosity based on information about attenuation of response sound signals and the estimated thickness for the location.

2. The method of claim 1, wherein identifying the estimated thickness for the location within the region and outside of the portion using the thickness profile comprises applying the thickness profile to the region in a direction perpendicular to a direction of thickness variation in the region.

3. The method of claim 1, wherein the thickness profile comprises thickness values for each location along a line, the line extending parallel to a direction of thickness variation in the region.

4. The method of claim 1 further comprising:
identifying an area having inconsistencies within the region of the composite structure based on the information about the attenuation of the response sound signals and the thickness profile.

5. The method of claim 1, wherein the portion of the region has desirable reflection from a second surface of the composite structure.

6. A method for inspecting a composite structure, the method comprising:
using a transducer to transmit ultrasonic waves at a portion of a region of the composite structure, the region having a cross-section with non-parallel surfaces;
identifying, using a processor, information about attenuation of response sound signals to the ultrasonic waves in the composite structure;
identifying, using a processor, an estimated thickness for a location outside the portion but within the region in the composite structure from a thickness profile of the region, the thickness profile comprising a plurality of thickness measurements of the portion of the region based on times of flight of the ultrasonic waves; and
identifying, using a processor, a porosity of the composite structure at the location based on the estimated thickness for the location and the information about the attenuation of the response sound signals at the location in the composite structure.

7. The method of claim 6, wherein identifying the estimated thickness for the location within the region from the thickness profile comprises applying the thickness profile to the region in a direction perpendicular to a direction of thickness variation in the region.

8. The method of claim 6, wherein the portion of the region has desirable reflection from a second surface of the composite structure.

9. The method of claim 6, wherein the thickness profile comprises thickness values for each location along a line, the line extending parallel to a direction of thickness variation in the region.

10. The method of claim 6 further comprising:
identifying an area having inconsistencies within the region of the composite structure based on the information about the attenuation of the response sound signals and the thickness profile.

11. An ultrasound inspection system for a composite structure, the ultrasound inspection system comprising:
a number of transducers configured to send sound signals into the composite structure and detect response sound signals to the sound signals sent into the composite structure; and
an analyzer in communication with the number of transducers, wherein the analyzer is configured to identify a thickness profile of a portion of a region of the composite structure, the region having a cross-section with non-parallel surfaces; identify an estimated thickness for a location within the region and outside of the portion using the thickness profile; and generate an indication of whether the location has undesirable porosity using the estimated thickness for the location and information about attenuation of the response sound signals detected by the number of transducers.

12. The ultrasound inspection system of claim 11, wherein identifying the estimated thickness for the location within the region and outside of the portion using the thickness profile comprises applying the thickness profile to the region in a direction perpendicular to a direction of thickness variation in the region.

13. The ultrasound inspection system of claim 11, wherein identifying the thickness profile comprises identifying thickness values for each location along a line, the line extending parallel to a direction of thickness variation in the region.

14. The ultrasound inspection system of claim 13, wherein identifying the thickness values for the each location along the line comprises identifying the thickness values using ultrasound inspection of the portion.

15. The ultrasound inspection system of claim 13, wherein identifying the thickness values for the each location along the line comprises identifying the thickness values from a model.

* * * * *